United States Patent
Balthasar et al.

(10) Patent No.: US 12,078,086 B2
(45) Date of Patent: Sep. 3, 2024

(54) METHOD FOR OPERATING A CHEMICAL PLANT

(71) Applicants: Wolff Balthasar, Ratingen (DE); Peter Ulrich Koss, Bad Homburg vor der Höhe (DE)

(72) Inventors: Wolff Balthasar, Ratingen (DE); Peter Ulrich Koss, Bad Homburg vor der Höhe (DE)

( * ) Notice: Subject to any disclaimer, the term of this patent is extended or adjusted under 35 U.S.C. 154(b) by 270 days.

(21) Appl. No.: 17/286,418

(22) PCT Filed: Oct. 17, 2019

(86) PCT No.: PCT/EP2019/078232
§ 371 (c)(1),
(2) Date: Apr. 16, 2021

(87) PCT Pub. No.: WO2020/083741
PCT Pub. Date: Apr. 30, 2020

(65) Prior Publication Data
US 2021/0301685 A1   Sep. 30, 2021
US 2022/0170389 A2   Jun. 2, 2022

(51) Int. Cl.
*F01K 23/06* (2006.01)
*C01B 3/02* (2006.01)
(Continued)

(52) U.S. Cl.
CPC ............ *F01K 23/064* (2013.01); *C01B 3/025* (2013.01); *C01C 1/0417* (2013.01);
(Continued)

(58) Field of Classification Search
CPC .......... F01K 23/064; F01K 3/188; F01K 7/22; F01K 11/02; C01B 3/025;
(Continued)

(56) References Cited

U.S. PATENT DOCUMENTS

| 4,340,820 | A | * | 7/1982 | Meyer-Pittroff | ...... F01K 13/006 290/51 |
| 4,942,734 | A | * | 7/1990 | Markbreiter | ........... F25J 1/0236 62/238.3 |

(Continued)

FOREIGN PATENT DOCUMENTS

EP   2395066 A1   12/2011

OTHER PUBLICATIONS

International Search Report for Application No. PCT/EP2019/078232, issued Nov. 11, 2019, 4 pages.

*Primary Examiner* — Loren C Edwards
(74) *Attorney, Agent, or Firm* — McCarter & English, LLP

(57) ABSTRACT

A chemical plant and operating method therefor; the chemical plant comprises a steam turbine having a shaft, a first pressure turbine stage and a second pressure turbine stage, each being arranged on the shaft and being connected in series in terms of the steam process; steam for driving the steam turbine is obtained from a reactor plant, said reactor plant producing a hydrogen-containing substance from a carbon-containing energy-carrier stream; the steam is heated in an overheating step before being supplied to the second pressure turbine stage; the steam turbine has a third pressure turbine stage which is arranged on the shaft and which is connected between the first pressure turbine stage and the second pressure turbine stage in terms of the steam process; and the steam passes through the overheating step after exiting the third pressure turbine stage.

13 Claims, 1 Drawing Sheet

(51) Int. Cl.
*C01C 1/04* (2006.01)
*C07C 29/152* (2006.01)
*F01K 3/18* (2006.01)
*F01K 7/22* (2006.01)
*F01K 11/02* (2006.01)

(52) U.S. Cl.
CPC ............ *C07C 29/152* (2013.01); *F01K 3/188* (2013.01); *F01K 7/22* (2013.01); *F01K 11/02* (2013.01); *C01B 2203/061* (2013.01); *C01B 2203/068* (2013.01); *C01B 2203/1614* (2013.01); *C01B 2203/1628* (2013.01); *C01B 2203/169* (2013.01)

(58) Field of Classification Search
CPC ........ C01B 2203/061; C01B 2203/068; C01B 2203/1614; C01B 2203/169; C01C 1/0417; C01C 29/152; F02C 6/18; C10J 3/00; C10J 3/56; C10L 3/08
See application file for complete search history.

(56) References Cited

U.S. PATENT DOCUMENTS

| | | | |
|---|---|---|---|
| 6,258,860 | B1 | 7/2001 | Weedon et al. |
| 6,588,212 | B1* | 7/2003 | Wallace .................... F02C 3/22 |
| | | | 60/39.12 |
| 2007/0000251 | A1* | 1/2007 | Isokawa ................. F01K 15/00 |
| | | | 60/645 |
| 2010/0170247 | A1* | 7/2010 | Bommareddy ......... C10K 1/101 |
| | | | 60/645 |
| 2011/0120127 | A1* | 5/2011 | Lippmann ................ F01K 7/22 |
| | | | 60/647 |
| 2015/0291438 | A1* | 10/2015 | Merritt ..................... C01B 3/36 |
| | | | 423/352 |

* cited by examiner

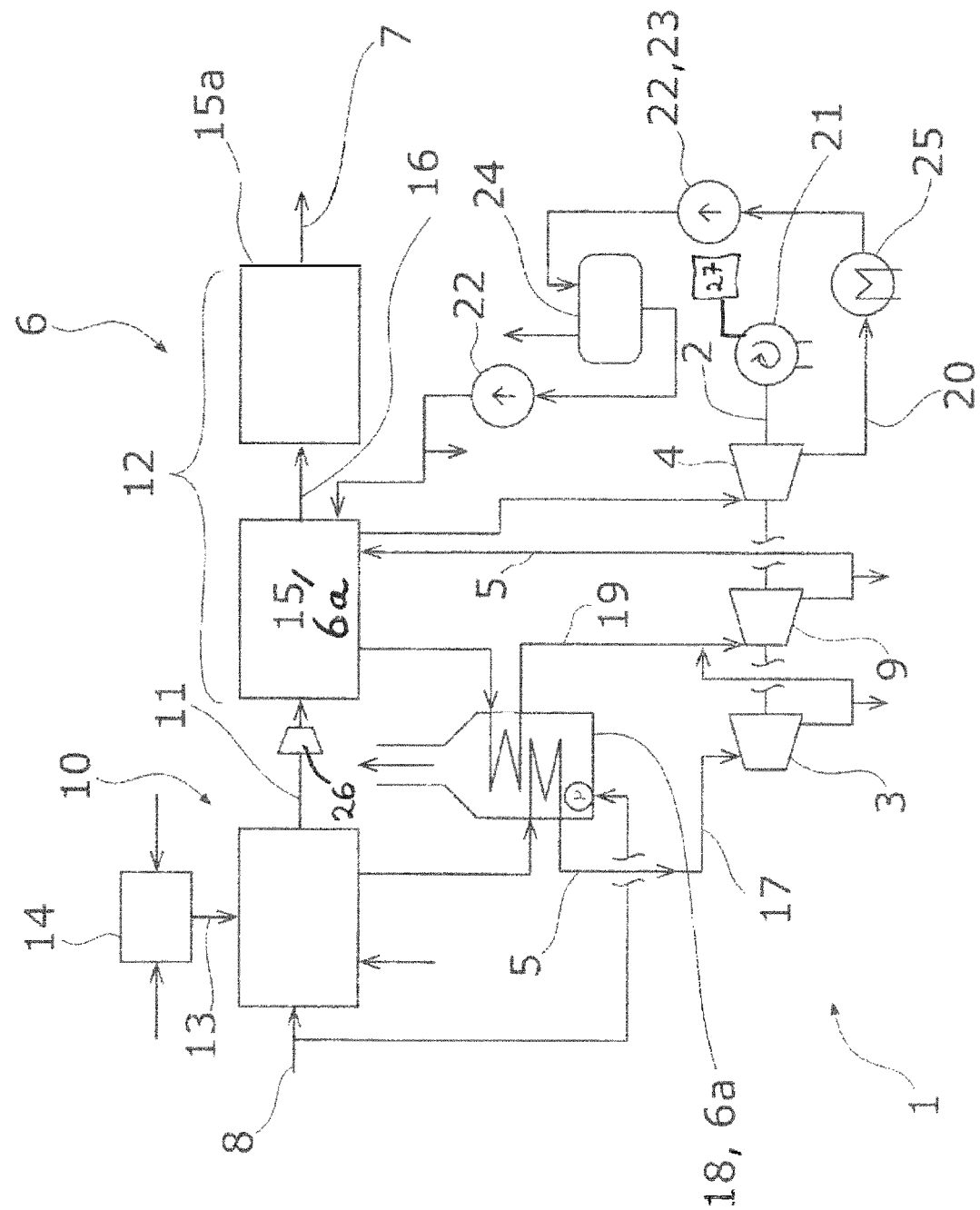

METHOD FOR OPERATING A CHEMICAL PLANT

CROSS-REFERENCE TO RELATED APPLICATIONS

This application is a U.S. national stage application of international application no. PCT/EP2019/078232 filed Oct. 17, 2019, entitled "Method for Operating a Chemical Plant," claiming priority under 35 U.S.C. § 119(a)-(d) to European application no. EP18202126.1 filed Oct. 23, 2018, which are hereby expressly incorporated by reference as part of the present disclosure.

FIELD OF THE INVENTION

The present disclosure relates to a method for operating a chemical plant as well as to a chemical plant.

BACKGROUND

Power generation by means of steam turbines is well-known from the prior art. As a rule, such a steam turbine has several pressure turbine stages disposed on a common shaft, which in turn drives a generator for power generation. The supplied and highly pressurized steam now successively passes through the individual pressure turbine stages for driving the shaft, the steam losing pressure by passing through the individual stages.

Overheating the steam not only before it is supplied for the first time to the steam turbine—and thus to the first pressure turbine stage—but also between the first pressure turbine stage and the one directly downstream thereof in order to improve in this manner the degree of efficiency of the steam turbine is also known from the prior art. Such an overheating process makes it possible to achieve a condensation of the exhaust steam in the final pressure turbine stage, by lowering the pressure almost to a vacuum. Condensing turbine of this type achieve a very high degree of efficiency, wherein up to 40% of the total output may result from this final pressure turbine stage.

However, steam turbines are not only used in power plants for power generation, where a single turbine generally generates a very high output, but are also employed, in smaller sizes, in plants of the chemical industry, which regularly produce process steam that may be used in a steam turbine. In such chemical plants, the steam turbine frequently drive mechanical devices directly, without an intermediate power generation step.

There are a variety of chemical plants, particularly synthesis plants, e.g. for the production of methanol or ammonia, in which a hydrogen-containing substance, such as hydrogen or synthesis gas, is produced from a carbon-containing energy-carrier flow, such as natural gas. In turn, the ultimately desired chemical substance can then be produced from such a synthesis gas, if necessary. In particular, smaller steam turbines, with which pumps and compressors of the chemical plant may then be driven, are also used in these chemical plants. The large number of required pumps and compressors results in the necessity of providing just as large a number of steam turbines. Because the dimensions of these steam turbines, owing to the smaller output required in each case, are smaller compared with those of the power generation steam turbines in power plants, they also have a smaller degree of efficiency in comparison.

Catalytic partial oxidation, which is also referred to as autothermic reforming, is a preferred manner of producing the synthesis gas in chemical plants. However, in the catalytic partial oxidation, the exiting synthesis gas, due to the supply of oxygen to the process, has such a large carbon monoxide partial pressure that a use of the synthesis gas for overheating the steam for the supply to the steam turbine appears not to be feasible in light of the current state of material sciences. For this high carbon monoxide partial pressure would result in a rapid destruction of the overheating device by metal dusting.

The consequence of this lack of an option for overheating by means of the synthesis gas, which is sufficiently hot as such, is that all the heat for overheating the steam has to be provided by a heating device fired with the natural gas—which is also referred to as a fired heater. In that case, the natural gas used for firing cannot be used for the synthesis, which reduces the yield of the plant.

SUMMARY

An object of the inventors was to develop a steam turbine in a chemical plant and a method for operating such a chemical plant in such a way that the steam turbine is able to provide its output for overheating the steam with a smaller consumption of natural gas or other energy carrier.

The inventors realized that, in a steam turbine in the context of a chemical plant, overheating the steam again between the pressure turbine stages—which process of repeated overheating is also referred to as reheating—can not only be carried out in the area of the high pressures, i.e. between the first two pressure turbine stages, but also in the area of lower pressures between the respectively subsequent pressure turbine stages. Though overheating in the case of such a procedure results in a slightly lower degree of efficiency than in the case of overheating at higher steam pressures, internal process heat of the chemical plant may then be used for overheating, so that the fired heating device is not required at least for this overheating process.

As a result, such a reheating offers the possibility of completely replacing in an economical manner the plurality of smaller steam turbines of the chemical plant with a single, correspondingly larger steam turbine for power generation, wherein the previously purely mechanically driven pumps and compressors of the chemical plant may then be driven electrically. The losses arising due to the intermediate conversion into electrical energy are then at least compensated by the improved degree of efficiency of the steam turbine.

This summary is not exhaustive of the scope of the present aspects and embodiments. Thus, while certain aspects and embodiments have been presented and/or outlined in this summary, it should be understood that the present aspects and embodiments are not limited to the aspects and embodiments in this summary. Indeed, other aspects and embodiments, which may be similar to and/or different from, the aspects and embodiments presented in this summary, will be apparent from the description, illustrations, and/or claims, which follow.

It should also be understood that any aspects and embodiments that are described in this summary and do not appear in the claims that follow are preserved for later presentation in this application or in one or more continuation patent applications.

BRIEF DESCRIPTION OF THE DRAWINGS

Other details, features, aims and advantages will become apparent from the following description and with reference to the Figure, which are understood not to be limiting.

FIG. 1 shows a schematic illustration of an embodiment of a chemical plant.

DETAILED DESCRIPTION

In at least one aspect, a method serves for operating a chemical plant illustrated in FIG. 1. The chemical plant has a steam turbine 1 with a shaft 2 and with a first pressure turbine stage 3 and a second pressure turbine stage 4. The first pressure turbine stage 3 and the second pressure turbine stage 4 are each disposed on the shaft 2 and connected in series in terms of the steam process. The connection in series of the first pressure turbine stage 3 and the second pressure turbine stage 4 in terms of the steam process means that turbine steam flowing through the steam turbine 1 for driving the shaft 2 first flows through the first pressure turbine stage 3 and only then through the second pressure turbine stage 4. In between, this turbine steam may in principle pass through any number of further pressure turbine stages of the steam turbine 1 or be supplied to another process. In at least some embodiments, the steam turbine 1 has an electrical maximum output of at least 30 MW, and in some embodiments an electrical maximum output of between 50 MW and 200 MW.

Steam 5 for driving the steam turbine 1 is obtained from a reactor plant 6, which reactor plant 6 produces a hydrogen-containing substance 7 from a carbon-containing energy-carrier flow 8, and wherein the steam 5 is heated in an overheating step prior to being supplied to the second pressure turbine stage 4. In at least some embodiments, the chemical plant includes the reactor plant 6. In this case, the overheating step may basically have an arbitrary duration and cause the steam 5 to be heated to a basically arbitrary temperature. In at least some embodiments, the steam 5 is heated to a temperature above the saturation temperature. The latter is the saturation temperature at the pressure that the steam 5 has in the overheating step. Heating may also take place in a basically arbitrary manner and fed by a basically arbitrary energy source.

The steam 5 is already heated when it is being obtained from the reactor plant 6, and thus prior to being supplied to the steam turbine 1—e.g., prior to being supplied to the first pressure turbine stage 3. In at least some embodiments, the steam 5 is heated to a temperature above the saturation temperature of the steam 5 prior to being supplied to the steam turbine 1—e.g., prior to being supplied to the first pressure turbine stage 3. Therefore, the heating prior to the supply to the second pressure turbine stage 4, at which point in time the steam 5 has already been supplied to the steam turbine 1, is a re-heating.

In the illustrated embodiment, the steam turbine 1 has a third pressure turbine stage 9 disposed on the shaft 2, which third pressure turbine stage 9 is connected between the first pressure turbine stage 3 and the second pressure turbine stage 4 in terms of the steam process. This means that turbine steam exiting the first pressure turbine stage 3 first flows through the third pressure turbine stage 9 before flowing through the second pressure turbine stage 4. Again, the turbine steam may in principle pass through any number of further pressure turbine stages or be supplied to another process, in each case between the first pressure turbine stage 3 and the third pressure turbine stage 9, and between the third pressure turbine stage 9 and the second pressure turbine stage 4.

The steam 5 passes through the overheating step after exiting the third pressure turbine stage 9. Thus, the steam 5 is heated in the overheating step prior to being supplied to the second pressure turbine stage 4.

The chemical plant includes the steam turbine 1, which in turn comprises the shaft 2, the first pressure turbine stage 3 and the second pressure turbine stage 4, wherein the first pressure turbine stage 3 and the second pressure turbine stage 4 are each disposed on the shaft 2 and connected in series in terms of the steam process.

The chemical plant further includes the reactor plant 6 for producing the hydrogen-containing substance 7 from the carbon-containing energy-carrier flow 8, wherein steam 5 for driving the steam turbine 1 is obtained from the reactor plant 6. The chemical plant also includes a heating assembly 6a for heating the steam 5 prior to it being supplied to the second pressure turbine stage 4. In principle, this heating assembly 6a may be any device or group of devices of the chemical plant, which may optionally also be included in the reactor plant 6.

In the chemical plant, the steam turbine 1 has a third pressure turbine stage 9, which is disposed on the shaft 2 and which is connected between the first pressure turbine stage 3 and the second pressure turbine stage 4 in terms of the steam process. In the chemical plant, the heating assembly 6a further heats the steam 5 subsequent to it exiting the third pressure turbine stage 9. Thus, a heating process takes place between the third pressure turbine stage 9 and the second pressure turbine stage 4.

In at least some embodiments, the steam 5 has a temperature of at least 450° C. prior to being supplied to the steam turbine 1—e.g., prior to being supplied to the first pressure turbine stage 3. Thus, the steam 5 is overheated. In at least some embodiments, the steam 5 may have a temperature of between 450° C. and 600° C. prior to being supplied to the steam turbine 1—e.g., prior to being supplied to the first pressure turbine stage 3. Accordingly, in at least some embodiments the steam 5 is heated in the overheating step to at least the temperature of the steam 5 prior to being supplied to the steam turbine 1—e.g., prior to being supplied to the first pressure turbine stage 3. In other words, the steam 5 is heated in the overheating step to a temperature of at least 450° C., and particularly to a temperature of between 450° ° C. and 650° C. With respect to the chemical plant, in at least some embodiments, the heating assembly 6a heats the steam 5 to a temperature of at least 450° ° C., and in some such embodiments to a temperature of between 450° C. and 650° C. Also, in at least some embodiments, the steam 5 has a pressure of between 1 bar and 20 bars when it is supplied to the second pressure turbine stage 4. In some such embodiments, the steam 5 may have a pressure of between 2 bars and 8 bars when it is supplied to the second pressure turbine stage 4.

Since the pressure of the steam 5 drops when it successively flows through the pressure turbine stages 3, 4, 9, the first pressure turbine stage 3 may also be referred to as a high-pressure turbine stage, the third pressure turbine stage 9 connected downstream of the first pressure turbine stage 3 may be referred to as a medium-pressure turbine stage, and the second pressure turbine stage 4 may be referred to as a low-pressure turbine stage. Thus, the steam 5 may, for instance, have a pressure of between 80 bars and 300 bars, e.g., between 100 bars and 200 bars, prior to flowing through the first pressure turbine stage 3. It is also the case in some embodiments that the steam 5, after flowing through the first pressure turbine stage 3 and prior to flowing through the third pressure turbine stage 9, has a pressure of between 30 bars and 100 bars, and finally a pressure of between 0.01 and 0.1 bars after flowing through the second pressure turbine stage 4. The steam overheated, upstream of the first pressure turbine stage 3 and upstream of the second pressure turbine stage 4, to a temperature of in this case more than 500° C. still has a temperature of, for example, between 15° C. and 40° C., or between 20° C. and 30° C., when exiting the second pressure turbine stage 4. It is also the case in some embodiments that the steam has a temperature of at least 280° C. or of substantially 280° ° C. when exiting the first pressure turbine stage 3.

In principle, the hydrogen-containing substance 7 may be any such substance. For example, the hydrogen-containing substance 7 may be hydrogen. The hydrogen-containing substance 7 may also be synthesis gas including carbon oxides and hydrogen. The hydrogen-containing substance 7 may also be a hydrogen-containing compound. In at least some embodiments, the reactor plant 6 produces methanol and, alternatively or additionally, ammonia. Accordingly, the hydrogen-containing substance 7 may be methanol or ammonia.

The reactor plant 6 may be divided into several sections with different functions in each case. Here, in at least some embodiments, synthesis gas 11, e.g., including hydrogen and carbon oxides, is obtained in a synthesis gas section 10 of the reactor plant 6. In at least some embodiments, the obtained synthesis gas 11 is supplied to a converting section 12 of the reactor plant 6 downstream of the synthesis gas section 10, in which converting section 12 the obtained synthesis gas 11 is converted into the hydrogen-containing substance 7. The synthesis gas 11 may include hydrogen and carbon oxides, or substantially consists thereof. In addition, the synthesis gas 11 may also contain nitrogen and smaller contents of noble gases, or contain hydrogen, carbon oxides, nitrogen and noble gases. In at least some embodiments, the synthesis gas 11 is converted in the converting section 12 into methanol and/or ammonia. For this conversion, other starting materials may also be supplied to the converting section 12, e.g. nitrogen for the production of ammonia. This may take place particularly if the synthesis gas 11 does not contain a sufficient amount of nitrogen.

In at least some embodiments, the carbon-containing energy-carrier flow 8 is supplied to the synthesis gas section 10 for obtaining the synthesis gas 11, that an oxygen-containing flow 13 is supplied to the synthesis gas section 10, and that the synthesis gas 11 is obtained in the synthesis gas section 10 through a catalytic partial oxidation—which may also be referred to as autothermal reforming—by means of the oxygen-containing flow 13. As is shown in FIG. 1, the oxygen-containing flow 13 may substantially consist of oxygen and be obtained from an air separation device 14 of the reactor plant 6.

In at least some embodiments, the steam 5 is heated in the overheating step by means of heat from a reaction during the conversion of the obtained synthesis gas 11 into the hydrogen-containing substance 7, e.g., into methanol and/or ammonia. For example, the reactions for forming methanol from synthesis gas 11 are exothermic, as is the reaction for obtaining ammonia from hydrogen and nitrogen, whereby the heat for heating the steam can thus be obtained. FIG. 1 shows that the steam 5 is guided from the steam turbine 1 to the converting section 12 for heating—e.g., to a reactor 15 of the converting section 12—and then back to the steam turbine 1. Accordingly, the reactor 15 in this case forms the heating assembly 6a. According to the illustration of FIG. 1, a product treatment unit 15a of the converting section, which obtains the hydrogen-containing substance 7 from the substance flow 16 exiting the reactor 15, is connected downstream of the reactor 15. In at least some embodiments, the product treatment unit 15a may be configured for obtaining the hydrogen-containing flow 7 from the substance flow 16 by purifying the substance flow 16.

In at least some embodiments, the converting section 12 has the reactor 15 with a catalyst for at least partially converting the synthesis gas 11 into the hydrogen-containing substance 7. The converting section 12 may also have a heat exchanger—not shown in FIG. 1 herein—for cooling the substance flow 16 from the reactor 15. The substance flow 16 can include a raw-product flow with the hydrogen-containing substance 7 and possibly non-reacted synthesis gas. In at least some embodiments, the steam 5 is heated in the overheating step by heat from the reactor 15 or the heat exchanger.

In at least some embodiments, the steam 5 supplied to the first pressure turbine stage 3 is already overheated and saturated. Therefore, a first saturated and overheated steam flow 17 may be supplied to the first pressure turbine stage 3 for driving the steam turbine 1. In principle, this first steam flow 17 may have any relationship with the steam 5. For example, the first steam flow 17 may be separate from the steam 5. However, the steam flow 17 may also include the steam 5 or consist thereof.

The overheating of the steam 5 for the first pressure turbine stage 3 may have a higher temperature than the downstream overheating between the third pressure turbine stage 9 and the second pressure turbine stage 4. Therefore, the exemplary embodiment shown here in FIG. 1 provides that the reactor plant 6 has a fired heating device 18, which overheats the steam 5, which is obtained in a saturated condition from the reactor plant 6, for obtaining the first steam flow 17. Apart from this overheating of the steam 5, the fired heating device 18 may also have further functions.

The heating device 18 may be fed by the carbon-containing energy-carrier flow 8. In at least some embodiments, the steam 5 is obtained in a saturated condition from the synthesis gas section 10. The steam 5 may be obtained from a process of draining water from the synthesis gas section 10, for example.

On the one hand, the steam turbine 1 may be operated such that all its pressure turbine stages 3, 4, 9 are operated substantially only by the steam 5 that is already being supplied to the first pressure turbine stage 3. However, it is also possible—as is shown in FIG. 1—to supply the pressure turbine 1 with additional steam downstream of the first pressure turbine stage 3. Accordingly, in at least some embodiments, a second, in particular saturated, steam flow 19 is obtained from the reactor plant 6, e.g., from the converting section 12, which is overheated by the heating device 18 and which is supplied to the third pressure turbine stage 9 for driving the steam turbine 1. As is shown in FIG. 1, that steam 5 exiting the first pressure turbine stage 3 is supplied to the third pressure turbine stage 9 for driving the steam turbine 1. Accordingly, the second steam flow 19 may be merged with the first steam flow 17 after the first steam flow 17 has exited the first pressure turbine stage 3. Pressures lower than those in the synthesis section 10 may occur in the converting section 12. Therefore, the second steam flow 19 from the converting section 12, which has a lower pressure compared with the first steam flow 17, may be merged with the first steam flow 17 if the first steam flow 17 has already lost some pressure by flowing through the first pressure turbine stage 3.

Also, a process steam flow, which may be a partial flow of the steam 5, may also be extracted after exiting from the first pressure turbine stage 3 or from the third pressure turbine stage 9. In at least some embodiments, the process steam flow is extracted prior to the supply to the third pressure turbine stage 9 of prior to the supply to the second pressure turbine stage 4. Such an extracted process steam flow is in at least some embodiments, supplied to the reactor plant 6. In at least some embodiments, the extracted process steam flow may be supplied to the reactor plant 6, and in at least some embodiments, to the synthesis gas section 10 or the converting section 12, and in the illustrated embodiment to the product treatment unit 15a. For example, the product treatment unit 15a may comprise distillation columns for product treatment. The latter regularly require greater steam quantities, which can accordingly be provided by the extracted process steam flow. The extracted process steam flow may be supplied as a heating medium and/or as a reaction medium in a chemical process.

Then, the process steam flow may be mixed with a process flow of the reactor plant 6. Alternatively, the process steam flow may be used as a heating medium in a reboiler of the chemical plant. In at least some embodiments, the process steam flow condensates in the process and is supplied as a condensate to the condensed water from the condenser 25—which is described in more detail below. As a consequence, the extracted process steam flow can no longer be returned to the steam turbine 1.

As is shown in FIG. 1, the steam turbine 1 may be a condensing turbine, so that condensation arises in the exhaust steam of, in particular, the second pressure turbine stage 4. Accordingly, in at least some embodiments, the second pressure turbine stage 4 relaxes the steam 5 supplied to it to form a wet steam 20. This permits achieving a very high degree of efficiency with the steam turbine 1.

Also in accordance with the illustration in FIG. 1, the chemical plant comprises a generator 21 for producing an electrical turbine current, which generator 21 is driven by the shaft 2. If, as in the present case, a steam turbine 1, and in particular a condensing turbine, is operated with several pressure turbine stages 3, 4, 9, then enough electrical power can be provided with it—and thus with a single steam turbine 1—in order to operate all, or at least vital, electrical consumers of the reactor plant 6. Possibly, excess electrical power generated by the generator 21 may even be provided to other consumers outside the reactor plant 6. In that case, it is no longer necessary to use a plurality of steam turbines with, in each case, lower power.

In principle, the turbine current may be used for an arbitrary purpose. In at least some embodiments, however, that the turbine current drives the air separation device 14 of the reactor plant 6. Also, the turbine current may drive a compressor assembly 26 and/or a pump assembly 22 of the reactor plant 6.

For example, it may also be advantageous that the air separation device 14 is powered electrically and that it can be operated additionally or exclusively with power from a power grid. The air separation device 14 may also produce, at least temporarily, oxygen for the oxygen-containing flow 13 and a surplus of oxygen beyond that. In other words, the air separation device 14 then produces more oxygen than is required by the chemical plant and particularly the synthesis gas section 10. In at least some embodiments, the oxygen surplus is then stored temporarily in a suitable storage unit, particularly in a liquid form.

This makes it possible for power from the power grid to be additionally consumed for the air separation device 14 specifically at those times or times of day when the price of electricity is low or even negative, while the reactor plant 6, and thus also the chemical plant, can continue to be operated. In times of higher electricity prices, the intermediately stored oxygen surplus can then be used to reduce the oxygen separation power and thus the power consumption of the air separation device 14. Thus, a power surplus is produced in the generator 21 which can be released to the power grid. A chemical plant equipped in this way can therefore take on the task of a buffer, also referred to as a peak shaver, which helps compensating the production and load fluctuations of a power grid as they may occur due to the integration of the regenerative power sources wind and photovoltaics. Comparatively large energy quantities can be stored in the form of oxygen in the manner described herein. This energy can then be returned in a targeted manner to the power grid by reducing the load of the air separation device 14.

With respect to the pump assembly 22, the pump assembly 22 may have a boiler water pump 23 for providing water for a boiler 24 of the reactor plant 6. This boiler 24 may be included in the converting section 12. According to the illustration of FIG. 1, the boiler water pump 23 may be supplied with water from the condenser 25 of the chemical plant, which condenser 25 is supplied with the wet steam 20.

With regard to the compressor assembly 26 the compressor assembly 26 may have a synthesis gas compressor for increasing the pressure in the reactor plant 6. As shown in FIG. 1, the compressor assembly 26, and also the synthesis gas compressor, may serve for increasing the pressure of the synthesis gas 11, i.e. particularly prior to being supplied to the reactor 15.

The compressors of a compressor assembly 26 and the pumps of a pump assembly 22 may be driven by electric motors. If the power from the electrical power supply grid is fed to the latter, adjusting their rotation speed becomes difficult. For the rotation speed of an electric motor first depends on the frequency of the current, which in the power supply grid is fixed at 50 Hz, for example. Providing a mechanical transmission for adjusting the respective rotation speed is expensive and requires a design which is both complex and laborious to maintain.

Therefore, in order to drive the compressor assembly 26 and the pump assembly 22 effectively, the chemical plant may have a frequency converter assembly 27 which, with a power electronic system of the frequency converter assembly 27, converts the turbine current, e.g., for driving the compressor assembly 26 and/or the pump assembly 22. In at least some embodiments, the chemical plant may have a frequency converter assembly 27 with an adjustable output frequency. In this case, the frequency converter assembly 27 may also have a plurality of individual frequency converters, e.g. at least one individual frequency converter is provided for each of the compressor assembly 26, the pump assembly 22 and for the air separation device 14. Thus, mechanical transmissions for these devices become dispensable. It was found that, due to progress in the field of frequency converters, this solution ultimately is economically more advantageous compared with mechanical transmissions, despite existing electrical losses and high costs.

Providing the frequency converter assembly 27 further permits the operation of the frequency converter assembly, and thus also of the compressor assembly 26, the pump assembly 22 and/or the air separation device 14, with power from the power supply grid when starting up the reactor plant 6, i.e. when steam 5 from the reactor plant 6 is not yet provided to a sufficient extent for operating the steam turbine 1.

While the above describes certain embodiments, those skilled in the art should understand that the foregoing description is not intended to limit the spirit or scope of the present disclosure. It should also be understood that the embodiments of the present disclosure described herein are merely exemplary and that a person skilled in the art may make any variations and modification without departing from the spirit and scope of the disclosure. All such variations and modifications, including those discussed above, are intended to be included within the scope of the disclosure.

The invention claimed is:

1. A method comprising:
a step of operating a chemical plant, wherein the chemical plant comprises a steam turbine defining a shaft, and a first pressure turbine stage, a second pressure turbine stage, and a third pressure turbine stage connected to the shaft in series, wherein the chemical plant comprises a reactor plant configured to produce a hydrogen-containing substance from a carbon-containing energy-carrier flow, wherein steam passing through the steam turbine successively passes through the first pressure turbine stage, the third pressure turbine stage and then the second pressure turbine stage;
wherein the operating step includes:
a step of generating a synthesis gas in a synthesis gas section of the reactor plant, wherein
the step of generating the synthesis gas includes:
supplying the carbon-containing energy-carrier flow to the synthesis gas section;
supplying an oxygen-containing flow to the synthesis gas section; and
generating the synthesis gas through an autothermal reforming using the oxygen-containing flow;
a step of converting the synthesis gas into the hydrogen-containing substance; and
a step of generating heat from a reaction during the converting step;
a step of obtaining steam from the reactor plant;
a step of driving the steam turbine with the steam;
a step of overheating the steam after the steam exits the third pressure turbine stage; and supplying said overheated steam to the second pressure turbine stage;
wherein the overheating step includes heating the steam with the heat from said reaction.

2. The method according to claim 1, further including the reactor plant producing methanol and/or ammonia.

3. The method according to claim 2, wherein the driving step includes supplying a first saturated and overheated steam flow to the first pressure turbine stage.

4. The method according to claim 3, wherein the reactor plant includes a fired heating device configured to overheat steam, and wherein the step of supplying the first steam flow includes
obtaining steam from the reactor plant in a saturated condition; and
overheating said steam in a saturated condition using the fired heating device.

5. The method according to claim 4, further including obtaining a second steam flow from the reactor plant; and
overheating the second steam flow using the fired heating device;
wherein the driving step includes supplying the second steam flow to the third pressure turbine stage without the second steam flow first passing through the first pressure turbine stage.

6. The method according to claim 1, wherein the reactor plant includes a converting section defining a reactor including a catalyst configured to at least partially convert the synthesis gas into the hydrogen-containing substance.

7. The method according to claim 1, wherein the steam turbine defines a condensing turbine, so that condensation forms in exhaust steam therefrom.

8. The method according to claim 1, wherein the chemical plant further comprises a generator configured to produce an electrical turbine current, and the method further includes driving the generator with the shaft.

9. The method according to claim 8, further including driving a pump assembly with the turbine current, wherein the pump assembly includes a boiler water pump configured to provide water for a boiler of the reactor plant.

10. The method according to claim 8, further including driving a compressor assembly with the turbine current, wherein the compressor assembly includes a synthesis gas compressor configured to increase pressure in the reactor plant.

11. The method according to claim 10, wherein the synthesis gas compressor is configured to increase pressure of the synthesis gas.

12. The method according to claim 8, wherein the chemical plant comprises a frequency converter configured to convert frequency of the turbine current.

13. A chemical plant comprising:
a steam turbine defining a shaft, and a first pressure turbine stage, a second pressure turbine stage, and a third pressure turbine stage connected to the shaft in series, wherein steam passing through the steam turbine successively passes through the first pressure turbine stage, the third pressure turbine stage and then the second pressure turbine stage;
a reactor plant configured to generate a synthesis gas in a synthesis gas section of the reactor plant from a carbon-containing energy-carrier flow and an oxygen-containing flow through autothermal reforming, to produce a hydrogen-containing substance from said synthesis gas, and to provide steam to drive the steam turbine; and
a heating assembly configured to heat the steam subsequent to the steam exiting the third pressure turbine stage and prior to the steam being supplied to the second pressure turbine stage with heat from a reaction during said production of the hydrogen-containing substance.

* * * * *